(12) United States Patent
Bansal et al.

(10) Patent No.: US 7,131,990 B2
(45) Date of Patent: Nov. 7, 2006

(54) PHOTOTHERAPY SYSTEM AND DEVICE

(75) Inventors: Vineet Bansal, Santa Clara, CA (US); Bryan Flaherty, Half Moon Bay, CA (US); Chris Chung, Dublin, CA (US)

(73) Assignee: Natus Medical Inc., San Carlos, CA (US)

( * ) Notice: Subject to any disclaimer, the term of this patent is extended or adjusted under 35 U.S.C. 154(b) by 109 days.

(21) Appl. No.: 10/265,970

(22) Filed: Oct. 7, 2002

(65) Prior Publication Data
US 2004/0068305 A1 Apr. 8, 2004

(51) Int. Cl.
*A61N 5/06* (2006.01)

(52) U.S. Cl. .......................... 607/90; 128/898; 607/94
(58) Field of Classification Search ............ 607/88–94; 128/898
See application file for complete search history.

(56) References Cited

U.S. PATENT DOCUMENTS

| | | | | |
|---|---|---|---|---|
| 4,907,132 A * | 3/1990 | Parker | .......................... | 607/88 |
| 5,299,109 A * | 3/1994 | Grondal | ....................... | 362/241 |
| 5,713,661 A * | 2/1998 | White | ......................... | 362/355 |
| 5,865,829 A * | 2/1999 | Kitajima | ........................ | 606/3 |
| 5,938,657 A * | 8/1999 | Assa et al. | ..................... | 607/89 |
| 6,045,575 A | 4/2000 | Rosen | | |
| 6,166,496 A | 12/2000 | Lys et al. | | |
| 6,290,713 B1 | 9/2001 | Russell | | |
| 6,325,793 B1 * | 12/2001 | Tomita | ........................ | 607/89 |
| 6,414,801 B1 * | 7/2002 | Roller | ........................ | 359/726 |
| 6,443,978 B1 * | 9/2002 | Zharov | ......................... | 607/91 |
| 6,464,714 B1 * | 10/2002 | Mewissen et al. | ............. | 607/90 |
| 6,596,016 B1 | 7/2003 | Vreman et al. | | |
| 6,663,659 B1 * | 12/2003 | McDaniel | ..................... | 607/88 |
| 6,669,684 B1 * | 12/2003 | Nakamura | ...................... | 606/5 |
| 6,796,690 B1 * | 9/2004 | Bohlander | .................. | 362/471 |
| 6,860,896 B1 * | 3/2005 | Leber et al. | .................... | 607/1 |
| 2003/0076281 A1 * | 4/2003 | Morgan et al. | ................ | 345/44 |
| 2003/0109907 A1 * | 6/2003 | Shadduck | ..................... | 607/89 |
| 2004/0022050 A1 * | 2/2004 | Yamashita et al. | ............. | 362/31 |
| 2004/0243198 A1 * | 12/2004 | Heacock et al. | .............. | 607/89 |
| 2004/0260365 A1 * | 12/2004 | Groseth et al. | ............... | 607/88 |

OTHER PUBLICATIONS

Seidman et al. *A New Blue Light -Emitting Phototherapy Device: A Prospective Randomized Controlled Study*, Journal of Pediatrics, Jun. 2000, vol. 136, No. 6, pp. 771-774.

Vreman et al. *Light-Emitting Diodes: A Novel Light Source for Phototherapy*, Pediatric Research, vol. 44, No. 5 (1998), pp. 804-809.

* cited by examiner

*Primary Examiner*—Henry M Johnson, III
(74) *Attorney, Agent, or Firm*—Mathew J. Temmerman

(57) ABSTRACT

A phototherapy system and device is disclosed, including an array of light sources arranged so as to achieve substantially uniform distribution of light on a subject. The light sources can be arranged in a number of configurations, including but not limited to distributions in which the density of lights sources is greater in the periphery than in the center. The present invention also includes a light diffusing panel to increase exposure uniformity, and a targeting mechanism to ensure that the device is properly aligned over the subject.

19 Claims, 5 Drawing Sheets

PHOTOTHERAPY SYSTEM AND DEVICE

BACKGROUND OF THE INVENTION

1. Field of the Invention

This invention relates to devices and methods for the phototherapeutic treatment of illness and diseases.

2. General Background

Phototherapy is a promising clinical tool for the treatment for many conditions, including seasonal affective disorder, bulimia nervosa, herpes, psoriasis, sleep disorders, acne, and skin cancer.

Phototherapy is especially promising as a treatment for hyperbilirubinemia, a common condition affecting 60–70% of all full-term infants. Hyperbilirubinemia is caused by the accumulation of excess bilirubin in the blood and skin of the infant. This excess bilirubin turns the skin and sclera a characteristic yellow color. If left untreated, extreme cases of hyperbilirubinemia can result in neurological insult (kernicterus) or even death. A common treatment for hyperbilirubinemia is phototherapy, in which the infant is exposed to light in a range corresponding to the peak absorption spectra for bilirubin (blue-green, 400–520 nm). This light changes the form of the bilirubin to a different isomer that is more readily eliminated by the body. The effectiveness of phototherapy depends on several factors: the spectrum of light delivered, the amount of surface area exposed to the light, the duration of the treatment, and the intensity of the light.

A number of different light sources can be used for phototherapy. Traditionally, broadband sources have been used, such as fluorescent, halogen, or incandescent light. However, it has been recently been suggested that light emitting diodes (LEDs) can be an effective phototherapeutic light source.

In the past, phototherapeutic light sources have been arranged into uniform arrays, typically in a rectangular pattern. Such a configuration can produce an acceptable average light intensity for phototherapy treatment. For instance, it has been found that a 10 inch by 20 inch array of approximately 750 blue LEDs suspended 12 inches above a subject can produce sufficient intensity, approximately 35 microwatts/cm2, in the spectrum of interest (400 nm to 520 nm), to be a clinically useful phototherapy device for the treatment of hyperbilirubinemia. However, there are a number of drawbacks to using such a simple rectangular array.

First, the distribution of light from a simple rectangular array will not be uniform. The intensity will be significantly higher underneath the center of the array than around the periphery. Thus, parts of the subject's skin will receive sufficient light intensity, but other parts will not, thereby limiting the effectiveness of the phototherapy.

Additionally, if the subject is not placed directly under the center of the array, he or she will not receive the full benefit of the delivered light energy. To address these concerns as they apply to phototherapy for jaundiced infants, the IEC (International Electronics Commission) has developed a standard that describes a method to measure the uniformity of phototherapeutic light. This standard also recommends that the ratio between lowest and highest intensity portions of the light delivered to the infant be greater than 0.4. See IEC 60601-2-50 (2000): "Medical Electrical Equipment— Part 2–50: Particular Requirements for the Safety of Infant Phototherapy Equipment."

SUMMARY OF THE INVENTION

The present invention is a phototherapy system including a non-uniform array of light sources, a clear light diffusing panel placed between the light sources and the subject, and a target mechanism to assist in positioning the subject underneath the center of the array. With these improvements, the present invention allows for a more uniform and precise phototherapeutic light exposure.

DETAILED DESCRIPTION

Figure 1:
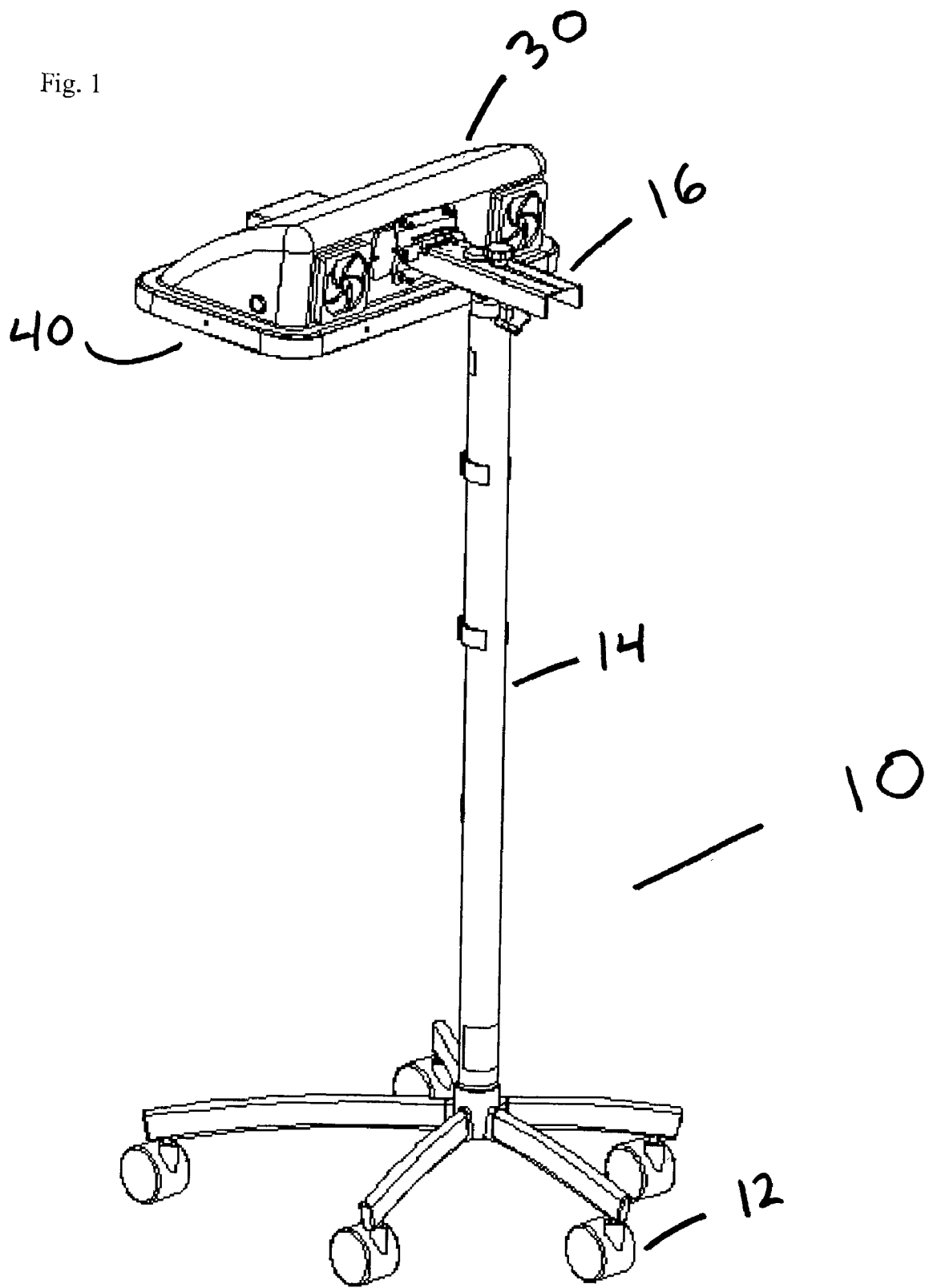
FIG. 1. is a perspective view of a device according to the present invention, with a stand.

The present invention is a phototherapy system and device, including (i) an optional stand 10, (ii) an enclosure 30 holding an array of light sources 40, (iii) a targeting mechanism 50 for use in centering the array over a subject, and (iv) a light diffusing panel 60 placed between the array 40 and a subject.

Figure 7:
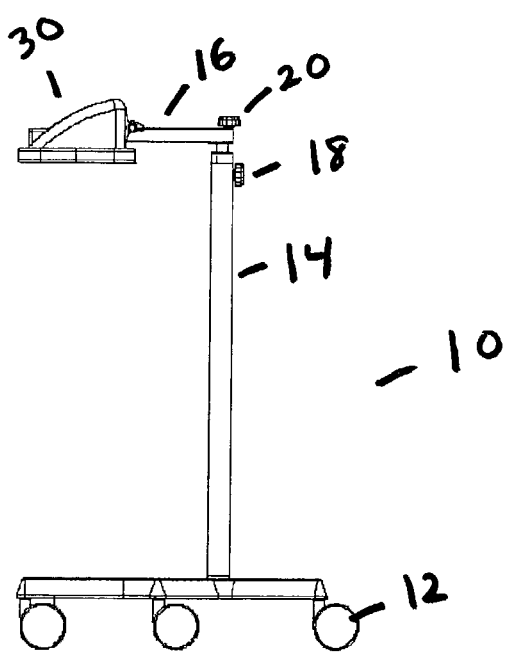
FIG. 7 is a side view of a device according to the present invention, with a stand.
Figure 8:
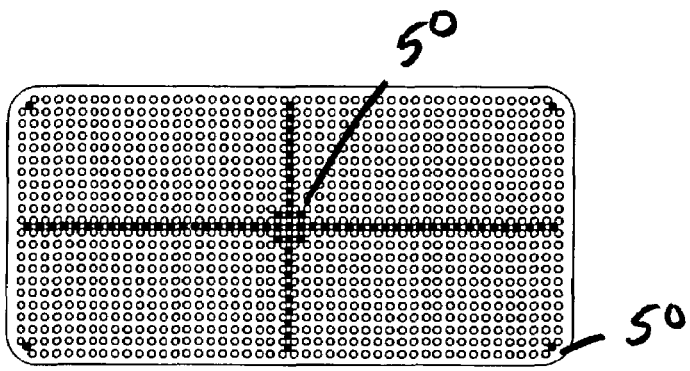
FIG. 8 depicts a targeting mechanism according to the present invention, along with an array of uniformly distributed light sources.

As depicted in FIGS. 1 and 7 the optional stand 10 is used to hold the light sources over the subject. The stand 10 may have wheels 12, a vertical extension 14, and a horizontal extension 16. It may also have height control means 18 to raise or lower the enclosure 30, and horizontal positioning means 20 to control the horizontal position of the enclosure 30. The stand is optional, and other means can be used to hold the array of lights over the subject. For instance, the array can be clipped or fastened over a bassinet, incubator or bed. Depending on the light source used, the array 40 can be distant or very close to the subject.

Figure 2:
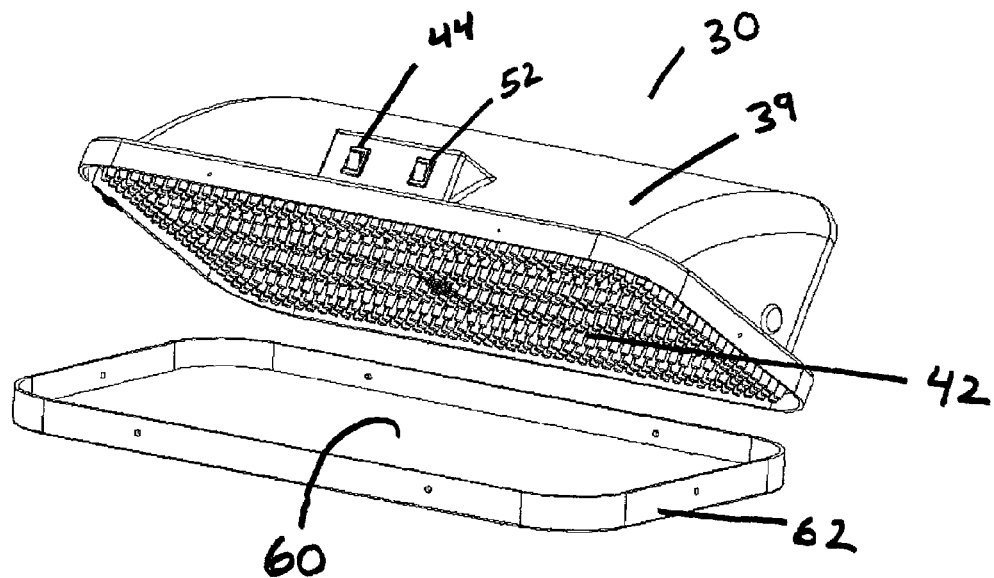
FIG. 2. is a perspective view of a device according to the present invention, without a stand, and with the enclosure tilted up to reveal exemplary LED light sources.
Figure 3:
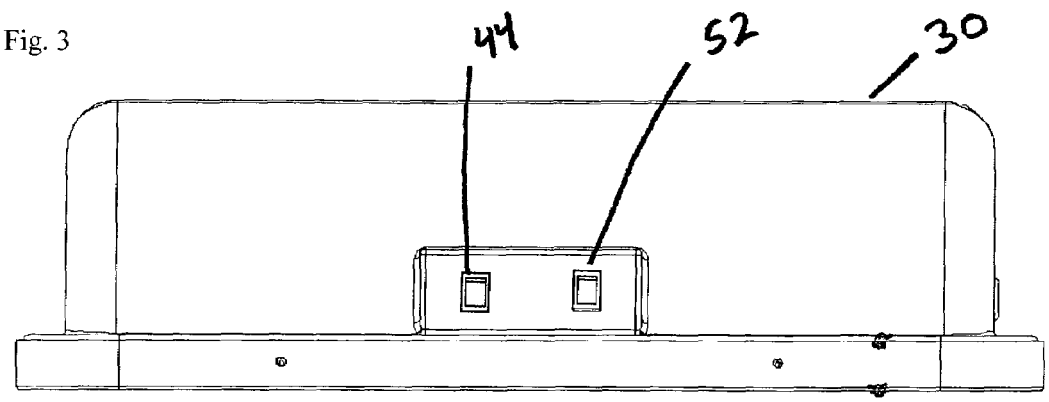
FIG. 3 is a front view of a device according to the present invention, without a stand.
Figure 4:
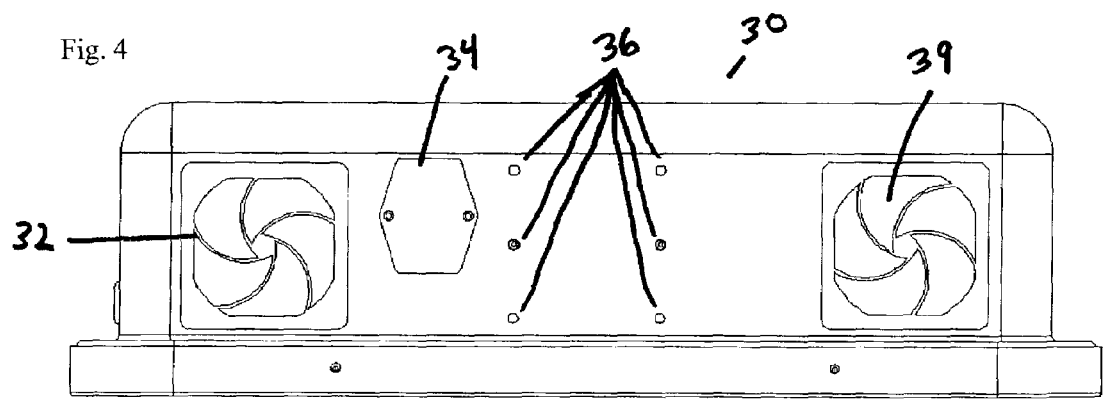
FIG. 4 is a back view of a device according to the present invention, without a stand.
Figure 5:
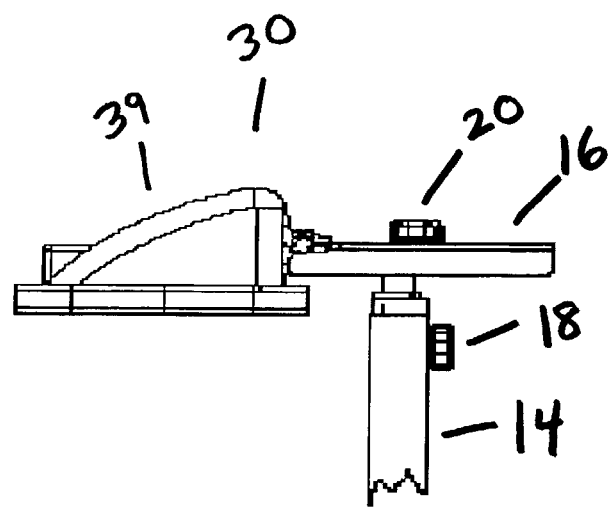
FIG. 5. is a side view of a device according to the present invention, without a stand.
Figure 6:
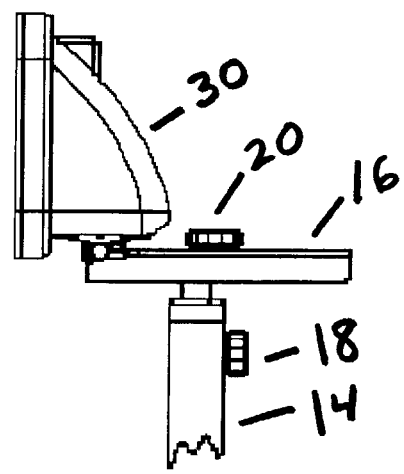
FIG. 6 is a side view of a device according to the present invention, without a stand, and with the enclosure tilted up.

The enclosure 30 can be mounted on the stand so that it can be easily tilted. (See FIG. 6). The enclosure 30 simply provides structural support for the sockets or board which hold the array of light sources 40. (For instance, FIG. 2 shows the enclosure 30 with an LED board 42). The precise form of the enclosure is irrelevant to the present invention. Indeed, for purposes of this patent, "enclosure" is defined to mean any structure that holds the light sources. As shown in FIGS. 2 & 4, at the back of the enclosure there is an exhaust 32, a power entry module 34, attachment plate 36 to attach the enclosure to the stand 10, an air inlet 38, and a top surface 39. The top surface 39 may be angled to discourage the placement of spillable liquids on the top of the device.

The enclosure can be made of many materials, such as metal or various kinds of plastic or polyvinyl materials. Typically, the enclosure will be a rigid structure. However, it is possible to use a flexible enclosure, to be used in embodiments in which the enclosure is wrapped around the subject.

The array of light sources 40 is a plurality of light sources, such as semi-conductor light sources, LEDs 42, halogen lights, incandescent lights, low-intensity lasers, etc. The array can take a number of different non-uniform forms to achieve the goal of even exposure on the subject's skin.

In one embodiment uniform exposure would result from selective removal or blocking of light sources from a previously uniform array. In another embodiment, the density of light source distribution would vary throughout the array, such as with a higher density in the periphery and a lower density in the center. In yet another version of the invention, low intensity light sources could be used in one portion of the array, and higher intensity light sources could be used in another section. This can be achieved by either using different intensity light sources or driving the light sources with a lower power in the center and a higher power on the outer edges. Another way that this can be achieved is by placing an absorber which varies in the degree of absorbance from the center to the outer circumference. This absorber can be placed in the path from the light source to the subject. Suitable absorbers include but are not limited to optical films and/or neutral density filters. Obviously, these various embodiments could be combined with each other. Some exemplary light source configurations are provided in FIGS. 9a–9d.

Switches are used to control the light sources, and in one embodiment, a switch 44 can provide for operation in either a high or low intensity mode or a potentiometer could be added to provide a more precise control or larger range on the intensity of phototherapy provided.

As stated above, broadband light sources include halogen, incandescent, fluorescent sources or certain types of semi-conductor light sources. Narrow-band sources include semi-conductor light sources, LEDs and low-intensity lasers. In one embodiment, approximately 750 blue-green (420–500 nm) LEDs can be used to treat hyperbilirubinemia. Such LEDs are commercially available from CREE, Inc. (4600 Silicon Drive, Durham, N.C. 27703) and Nichia America Corporation (3775 Hempland Road, Mountville, Pa. 17554). The number of light sources in the array will vary based on their intensity and the nature of the phototherapeutic treatment.

Typically, the light sources 40 would shine down on the subject. However, they can also be oriented upwards, and bounce off an optional mirror on the enclosure. Such a mirror can be curved into a convex formation, to diffuse the light away from the center of the subject Also, the light sources can be arranged to shine from the side, such as through a transparent bassinet, or even from the bottom.

The targeting mechanism 50 provides a means to center the array over the subject, thereby maximizing the effectiveness of the phototherapy. The targeting mechanism may be any light, such as a sub-array of LED-s, a low-intensity laser, or an incandescent source, so long as the light is capable of producing a visible beam or area on the subject. A switch 52 can control whether the target light is on or off.

Figure 9A:
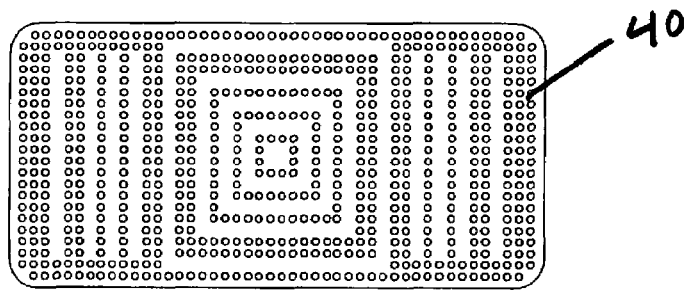
FIGS. 9a–9d show exemplary light source configurations according to the present invention.
Figure 9B:
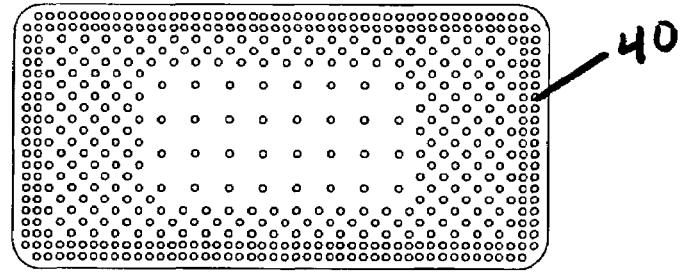
Figure 9C:
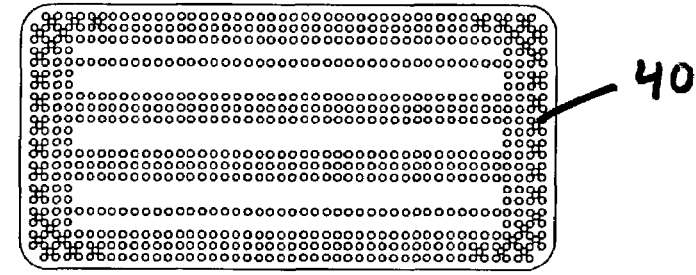
Figure 9D:
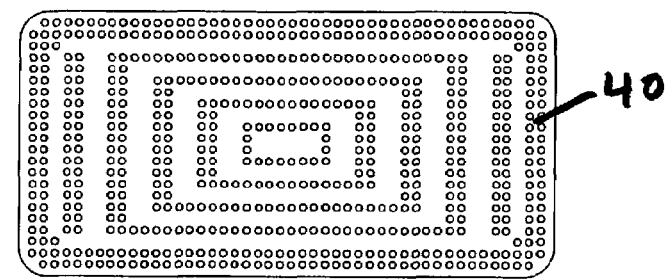
Figure 10A:
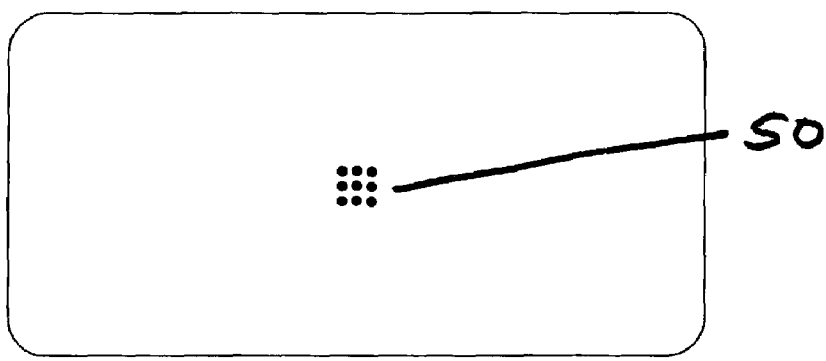
FIGS. 10a–10d show exemplary targeting mechanisms according to the present invention.
Figure 10B:
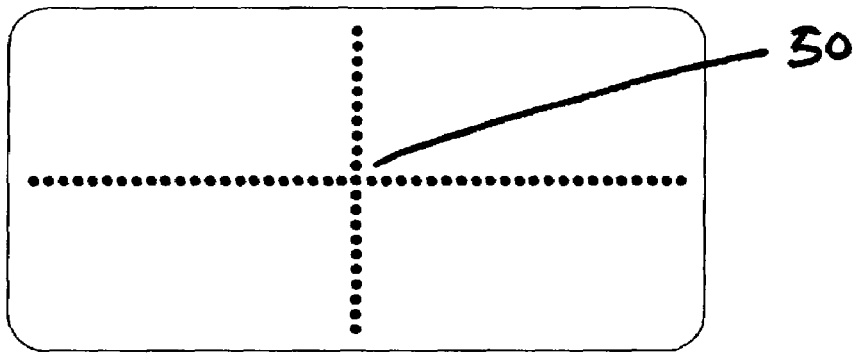
Figure 10C:
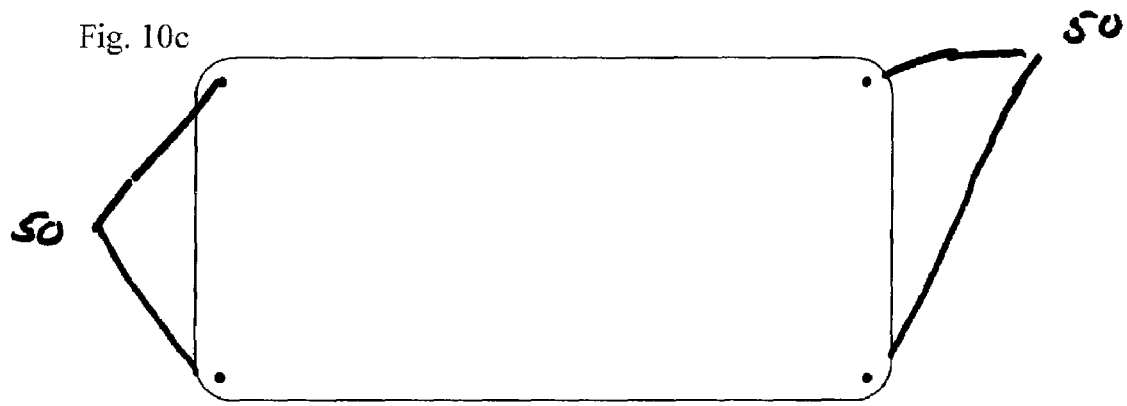
Figure 10D:
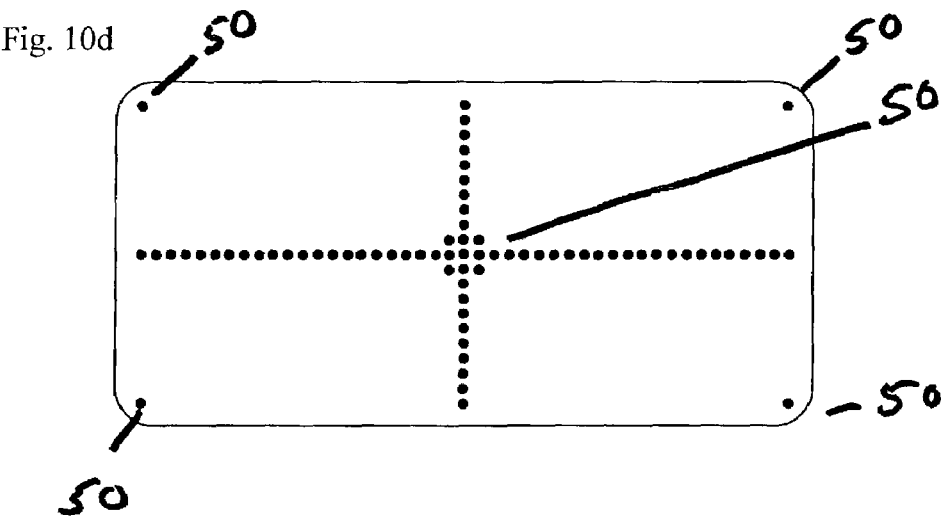

Exemplary targeting mechanisms include but are not limited to the following (i) n set of lights in the center of the array (FIG. 10a), (ii) a "cross-hair" formation of lights (FIG. 10b), (iii) corner lights (FIG. 10c), or (iv) a combination of these mechanisms (FIGS. 9 & 10d). The targeting mechanism light can be the same color as the rest of the array, or a different color, and it can be either the same intensity or a different intensity from the rest of the lights in the array. Indeed, the targeting mechanism need not be separate from the remainder of the array; the targeting mechanism may simply be a control circuit that illuminates certain lights separately from the rest of the array, so that those lights can serve a targeting function. In one embodiment, the target lights take the form of a small array of red LEDs (such as part #92F2646 from Newark Electronics) positioned in an array of blue phototherapy LEDs. Under this embodiment, the red LEDs can be illuminated by the clinician through a switch.

The targeting mechanism 50 need not be a light source. For instance, a retractable cord extending from the center of the array could be used to align the light sources with the subject. Alternatively, an optical targeting mechanism, similar to a gun sight, could be used to center the light sources. In this embodiment, mirrors and lenses and would form an optical path whereby the operator would visually align the light sources over the subject.

The light diffusing means 60 is placed within the path that light travels from the light sources 40 towards the subject. Typically, this means that the light diffusing panel is placed between the light sources and the subject, but if the lights are reflected onto a mirror, the panel can be placed between the light sources and the mirror. For purposes of this patent, the phrase "between said light sources and said subject" includes any placement under which the light from the light sources travels through the light diffusing means before hitting the subject.

The purpose of the light diffusing mechanism is to diffuse the point light sources to create a more even, uniform distribution of light. The light diffusing panel 60 can be made from any number of materials, so long as the panel allows light in the wavelength of interest to pass through, and so long as the material diffuses the light. Clear or colored plastic or glass panels with surface features have proven to be effective. The panel can have embedded diffusers such as bubbles, metal oxides, or materials with different refractive indices from the panel. Other diffusing materials include fibrous materials such as glass or plastic fibers. Commercially available diffusers such as "roma clear," "prismatic clear," "cracked ice," "box prismatic," "glacial," and "obscure" can used. The diffusing medium can be held in place by a bezeled cover 62.

The light diffusing panel 60 not only enhances the effectiveness of phototherapy by providing more even exposure, but it also improves safety and comfort, since diffuse light may be gentler to the eyes than focused light. Thus, when used with opaque eye shields, the light diffusing panel 60 may provide a complementary layer of protection for the subject. The panel may also improve the safety and comfort of bystanders who incidentally view light from the array 40. Additionally, the light diffusing panel may prevent debris from falling onto the subject.

In operation, the subject may be placed under the phototherapy device, and the target mechanism is used to align the array of light sources over the subject. Typically, the subject or the array is moved so that the target light is centered on the subject's chest or abdomen.

One skilled in the art will appreciate that the present invention can be practiced through a number of embodiments, including but not limited to those specifically described in this patent. Therefore, the embodiments, dimensions, and materials described in this patent are presented for illustration, not to limit the scope of the claims.

We claim:

1. A phototherapy device, comprising a plurality of phototherapeutic light sources of substantially the same wavelength distributed into an array, wherein the physical placement of said light sources within said array is non-uniform and wherein said array has a peripheral area with a first density of light sources, and a central area with a second density of light sources, and wherein the light sources are distributed so that said first density is higher than said second density.

2. The device according to claim 1, wherein said light sources are LEDs.

3. The device according to claim 2, wherein said LEDs emit light with a wavelength in the range of 400–520 nm.

4. A phototherapy device, comprising a plurality of phototherapeutic light sources of substantially the same wavelength distributed into an array, wherein the physical placement of said light sources within said array is non-uniform and wherein said light sources are arranged as shown in FIG. 9a.

5. A phototherapy device, comprising a plurality of phototherapeutic light sources of substantially the same wavelength distributed into an array, wherein the physical placement of said light sources within said array is non-uniform and wherein said light sources are arranged as shown in FIG. 9b.

6. A phototherapy device, comprising a plurality of phototherapeutic light sources of substantially the same wavelength distributed into an array, wherein the physical placement of said light sources within said array is non-uniform and wherein said light sources are arranged as shown in FIG. 9c.

7. A phototherapy device, comprising a plurality of phototherapeutic light sources of substantially the same wavelength distributed into an array, wherein the physical placement of said light sources within said array is non-uniform and wherein said light sources are arranged as shown in FIG. 9d.

8. A phototherapy device, comprising
an array of phototherapeutic blue light sources having a center; and
a targeting mechanism for positioning said array of blue light sources on a subject wherein said targeting mechanism comprises an array of red light sources in the center of said array of blue light sources.

9. The phototherapy device according to claim 8, wherein said array of blue light sources has a first intensity and said array of right light sources has a second intensity different from said first intensity.

10. The phototherapy system according to claim 8, wherein said array of red light sources produces a visible area of light on said subject.

11. The phototherapy system according to claim 8, wherein said targeting mechanism comprises an LED.

12. A phototherapy device, comprising:
a first array of phototherapeutic light sources; and
a targeting mechanism for positioning said first array of light sources on a subject;
wherein:
said targeting mechanism comprises a second array of light sources;
said first array emits light of a first color;
said second array emits light of a second color; and
said first color is not the same as second color.

13. A phototherapy device, comprising:
a first array of light sources, wherein the physical placement of said light sources within said first array is non-uniform; and
a targeting mechanism for positioning said array of light sources on a subject;
wherein:
said targeting mechanism comprises a second array of light sources;
said first array emits light of a first color;
said second array emits light of a second color; and
said first color is not the same as second color.

14. The device according to claim 13, wherein said light sources are LEDs.

15. The device according to claim 14, wherein said LEDs emit light with a wavelength in the range of 400–520 nm.

16. A phototherapy method for treating a condition comprising exposing a subject to light emitted from a plurality of light sources organized into a first array, wherein the physical placement of said light sources within said first array is non-uniform; positioning said plurality of light sources using a targeting mechanism wherein:
positioned using a targeting mechanism wherein:
said targeting mechanism comprises a second array of light sources;
said first array emits light of a first color;
said second array emits light of a second color; and
said first color is not the same as second color.

17. The method according to claim 16, wherein said method is used to treat hyperbilirubinemia.

18. A phototherapy method for treating a condition, comprising:
providing a plurality of light sources organized into an array, wherein the physical placement of said light sources within said array is non-uniform;
positioning a subject under said array of light sources using a targeting mechanism;
diffusing light from said light sources; and
exposing said subject to said diffused light from said array.

19. The method according to claim 18, wherein said method is used to treat hyperbilirubinemia.

* * * * *